United States Patent [19]
Louw et al.

[11] Patent Number: 5,527,327
[45] Date of Patent: Jun. 18, 1996

[54] VALVULOTOME

[75] Inventors: Jacob F. R. Louw, Carlsbad; Henry Garza, Vista, both of Calif.

[73] Assignee: Intramed Laboratories, Inc., San Diego, Calif.

[21] Appl. No.: 328,559

[22] Filed: Oct. 25, 1994

Related U.S. Application Data

[63] Continuation of Ser. No. 218,463, Mar. 28, 1994, abandoned, which is a continuation of Ser. No. 895,110, Jun. 8, 1992, abandoned.

[51] Int. Cl.⁶ .................................................. A61B 17/32
[52] U.S. Cl. ............................................................ 606/159
[58] Field of Search ................................. 606/159, 171

[56] References Cited

U.S. PATENT DOCUMENTS

| | | | |
|---|---|---|---|
| 3,837,345 | 9/1974 | Matar | 606/159 |
| 4,768,508 | 9/1988 | Chin et al. | 606/159 |
| 4,771,774 | 9/1988 | Simpson et al. | 606/171 |
| 5,026,383 | 6/1991 | Nobles | 606/159 |
| 5,041,082 | 8/1991 | Shiber | 606/159 X |
| 5,047,041 | 9/1991 | Samuels | 606/159 |
| 5,069,679 | 12/1991 | Taheri | 606/159 |
| 5,092,872 | 3/1992 | Segalowitz | 606/159 |

FOREIGN PATENT DOCUMENTS

| | | | |
|---|---|---|---|
| 2044103 | 10/1980 | United Kingdom | 606/159 |

*Primary Examiner*—Michael H. Thaler
*Attorney, Agent, or Firm*—Freilich Hornbaker & Rosen

[57] ABSTRACT

An improved valvulotome structure characterized by an elongate flexible shaft having proximal and distal ends and a cylindrical cutting member externally mounted around said shaft for axial movement, relative to said distal end, between a retracted and an extended position.

15 Claims, 6 Drawing Sheets

VALVULOTOME

This application is a continuation of application Ser. No. 08/218,463, filed Mar. 28, 1994, now abandoned, which is a continuation of application Ser. No. 07/895,110, filed Jun. 8, 1992, now abandoned.

BACKGROUND OF THE INVENTION

The present invention is directed to valvulotomes useful in medical procedures for removing valves from veins.

Techniques have been developed to reduce the invasiveness of bypass surgery to treat peripheral vascular disease blocking a patient's artery. Traditionally, a large incision is made in the patient's leg through which either a synthetic graft or a vein of the patient taken from another place in the body is inserted to bypass a diseased section of artery. A minimally invasive alternative is to use one of the patient's veins in place, or in situ, for the bypass. However, in order for this procedure to be effective, the valves of the vein ("venous" valves), which normally prevent reverse blood flow, must be removed. Angioscopy, i.e., the visual observation of the interior of a blood vessel by use of an endoscope inserted into the vessel, is preferably used by the surgeon during the valve removal procedure to optimize its efficacy and minimize vein damage.

The use of valvulotomes for cutting or disrupting vein valves, is discussed in the prior art. For example, only see:

| | |
|---|---|
| Segalowitz | U.S. Pat. No. 5,092,872 |
| Nobles | U.S. Pat. No. 5,026,383 |
| Chin | U.S. Pat. No. 4,739,760 |
| Leather | U.S. Pat. No. 4,493,321 |

In a typical valve removal procedure, a first end of a pulling catheter is inserted through a distal vein incision and advanced through the vein until it exits from a proximal vein incision. Because normal blood flow through the vein is in a distal to proximal direction, the pulling catheter moves past the valves by simply pushing the valve leaflets aside in their natural direction of motion.

At the site of the proximal vein incision, the pulling catheter first end is attached to a valvulotome distal end. The pulling catheter is then pulled back through the vein enabling cutting edges on the valvulotome to cut the valve leaflets. Progress of the valvulotome through the vein can be monitored on a viewing scope near the proximal end of the valvulotome which displays an image captured at the valvulotome distal end.

In order to minimize vein wall damage, it is preferable to configure the valvulotome to prevent contact between the cutting edge and vein wall while the valvulotome is advancing through the vein. It is also desirable to maximize the field of view available in the imaging window at the valvulotome distal end.

SUMMARY OF THE INVENTION

The present invention is directed to an improved valvulotome structure characterized by an elongate flexible shaft having proximal and distal ends. A cylindrical cutting member is externally mounted around, i.e., radially outward of said shaft for axial movement, relative to said shaft distal end, between a retracted and an extended position.

In the retracted position, the view angle of an imaging window defined at the shaft distal end is maximized. Additionally, the cutting member hugs a guide surface on the shaft to prevent its cutting edge from damaging the vein wall as it is pulled through the vein. In the extended position, the cutting edge is exposed and readily visible in the imaging window thereby facilitating proper alignment of the cutting edge with valve leaflets in the vein.

A user operable actuator means is mounted on the shaft enabling a surgeon to selectively move the cutting member to the extended position.

In a preferred embodiment, the cutting member comprises a ring having two cutting blades cantilevered in an axial direction therefrom. The ring is mounted on the shaft with the blades extending distally. Interior surfaces of the cutting blades engage guide surfaces formed on the shaft proximate to its distal end. The ring is bonded to the distal end of an outer sleeve mounted for reciprocal movement along the elongate shaft. Thus, by moving the sleeve, the cutting member can be moved between the aforementioned retracted and extended positions.

The shaft preferably accommodates at least two elongate optical fibers, the first fiber to illuminate the vein interior at the shaft distal end and the second fiber to transfer an image from the distal end to a video camera for viewing on a monitor, at the shaft proximal end. The shaft also preferably defines a working channel which can, for example, be used to transfer fluid for irrigation and/or aspiration. A multipurpose connector body is mounted on the proximal end of the shaft with suitable terminations for the optical fibers and the working channel.

The optical fibers and working channel are terminated at the shaft distal end in a shaft head where they are preferably bonded together by a suitable potting material. A blade guide is preferably externally mounted on the shaft proximate to its distal end and defines the aforementioned guide surface. A filament secured to the blade guide extends to a connector used for detachable attachment to a separate pulling catheter.

Embodiments of the invention find particular utility as cost effective, single-use, valvulotomes that afford excellent viewing conditions during movement of the valvulotome along the vein and during cutting of vein valves while simultaneously protecting the vein wall and tributaries from damage by the valvulotome's cutting edges.

DETAILED DESCRIPTION

Figure 1A:
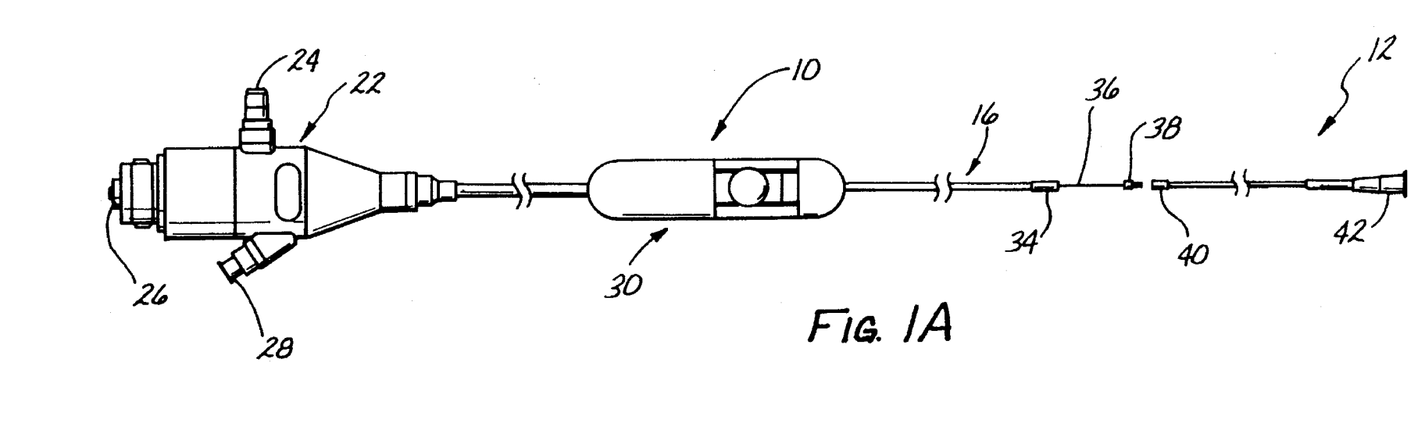
FIG. 1A is a schematic top plan view of a valvulotome and pulling catheter in accordance with the present invention.
Figure 1B:
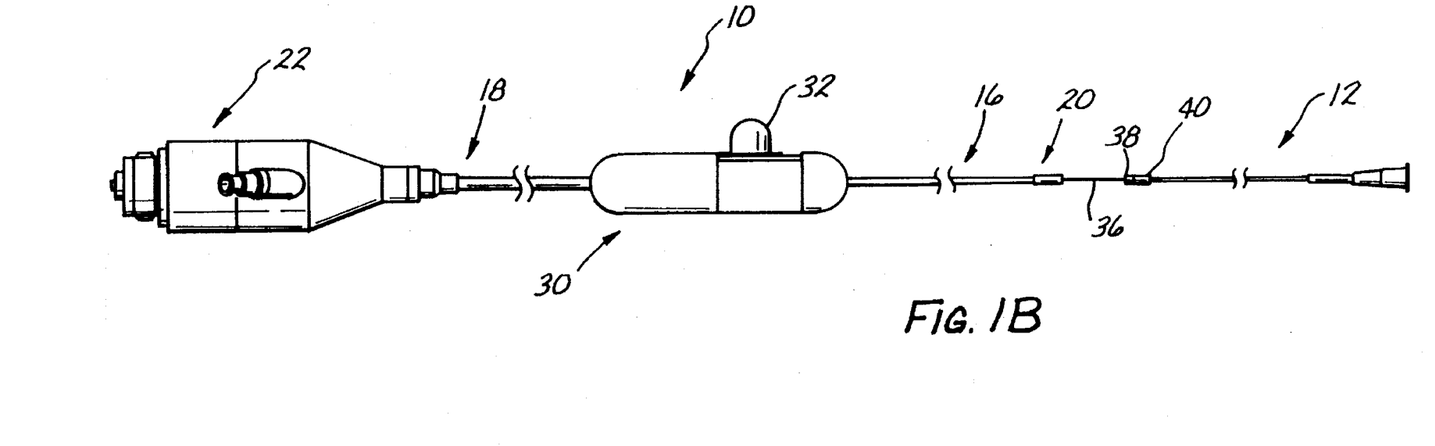
FIG. 1B is a side view corresponding to FIG. 1A.

Attention is initially directed to FIGS. 1A and 1B which depict a valvulotome 10 in accordance with the present invention together with a pulling catheter 12 adapted to be used with the valvulotome as depicted in FIGS. 2A–2D for the purpose of removing valves from veins.

Briefly, the valvulotome 10 is comprised of an elongate shaft 16 having a proximal end portion 18 and a distal end portion 20. A multipurpose connector body 22 is mounted on the shaft proximal end 18 and houses a plurality of connector fittings including a light source connector 24, a camera coupler 26 and luer fitting 28. A handle body 30 is mounted on the shaft 16 between the proximal and distal end portions 18, 20. A blade actuation slide member 32 is carried by the handle body and is used by a surgeon to selectively move a cutting member 34, located proximate to the shaft end portion 20 between a retracted position and an extended position.

Extending from the shaft distal end portion 20 is a filament 36 which is attached to a connector 38. The connector 38 is configured for detachable attachment to a connector 40 affixed to a first end of the pulling catheter 12. A luer fitting 42 is formed on the pulling catheter second end. It is pointed out that FIG. 1A shows the valvulotome connector 38 and pulling catheter connector 40 unattached. FIG. 1B depicts the connectors 38 and 40 after they have been attached. It should also be noted that FIG. 1A depicts exemplary dimensions for a preferred embodiment of the invention.

Figure 2A:
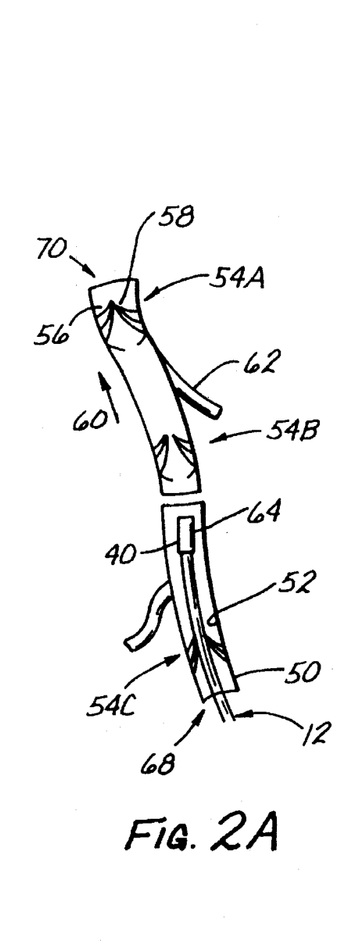
FIGS. 2A through 2D are schematic representations depicting the use of a valvulotome in accordance with the present invention.

Before proceeding to a detailed description of the valvulotome structure, as depicted in FIGS. 3–7, attention is directed to FIGS. 2A–2D which show a typical vein valve cutting procedure utilizing a valvulotome constructed in accordance with the present invention. FIG. 2A schematically shows a vein 50 having an inner wall 52 which supports valves 54 (shown as 54A, 54B, and 54C). Each of the valves 54 is comprised of valve leaflets 56, 58. The normal direction of venous blood flow is represented by arrow 60 in FIG. 2A. In addition to the valve leaflets 56, 58, note also that FIG. 2A depicts side tributaries 62 which communicate with the interior of the vein 50 through the vein wall 52.

Figure 2B:
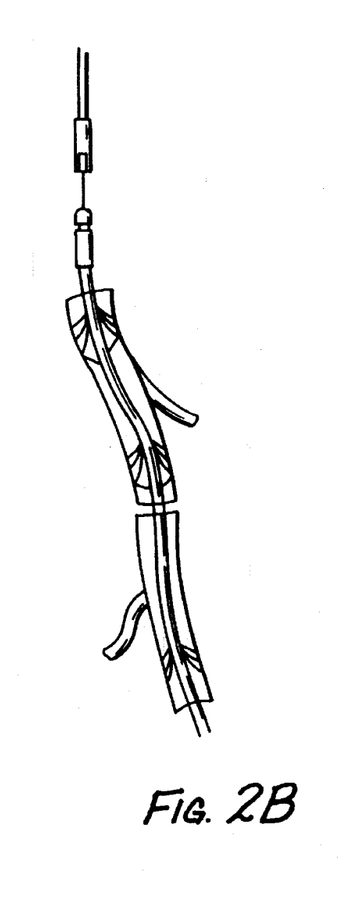
Figure 2C:
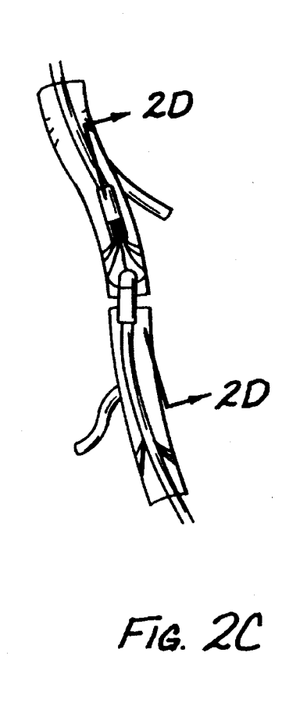

In a preferred utilization of a valvulotome in accordance with the invention, the first end 64 of the pulling catheter 12, carrying connector 40, is inserted into the vein 50 via a distal vein incision 68. The pulling catheter 12 is pushed through the vein 50 in the normal direction of venous blood flow until its first end 64 exits through a proximal vein incision 70. This is shown in FIG. 2B which also shows the pulling catheter connector 40 being attached to the valvulotome connector 38. With the pulling catheter and the valvulotome connected as shown in FIG. 2B, the pulling catheter is then pulled back through the vein 50 in a direction opposite to normal venous blood flow.

Figure 2D:
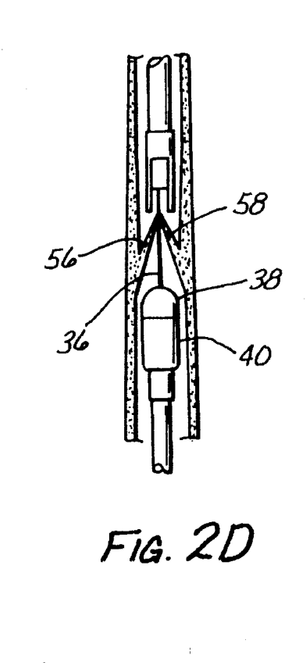

As will be seen hereinafter, the valvulotome 10 in accordance with the invention includes an optical imaging fiber extending from the shaft distal end 20 to enable a surgeon to view the vein interior via a viewing device, e.g., a video camera and monitor (not shown), connected to camera coupler 26, as the valvulotome is being pulled through the vein. As the cutting member 34 approaches the vein valves to be cut, the surgeon can extend the blades, as shown in FIG. 2D, optimally position and orient the blades relative to the valve leaflets. When so positioned and oriented, the surgeon can then pull the pulling catheter and valvulotome distally to cause the blade cutting edges to clearly cut the valve leaflets.

Figure 3A:
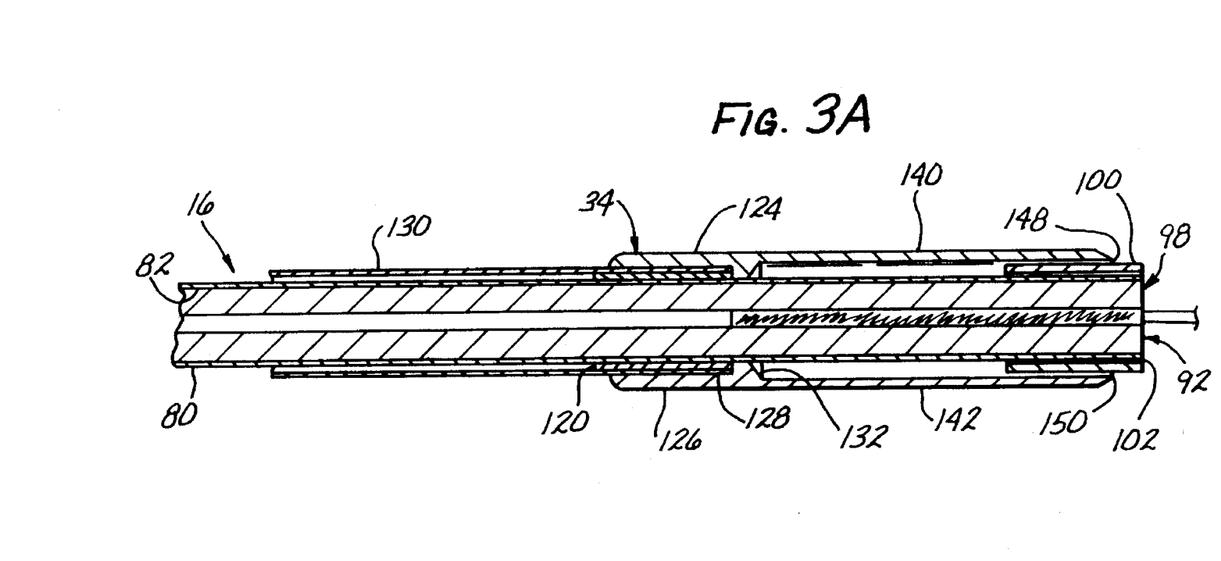
FIGS. 3A and 3B are sectional view through the distal end portion of the valvulotome shaft showing the cutting member in its retracted position and its extended position, respectively.
Figure 3B:
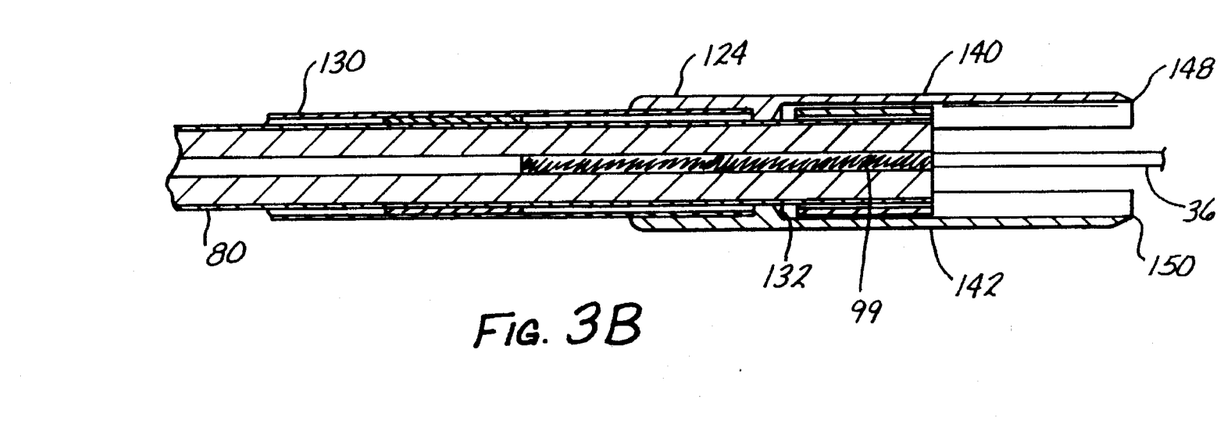
Figure 4:
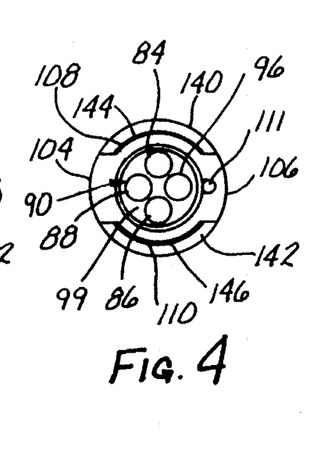
FIG. 4 is a schematic end view of the valvulotome depicted in FIGS. 3A and 3B.

Attention is now directed to FIG. 3A which shows an enlarged sectional view through the distal end portion 20 of valvulotome shaft 16. The valvulotome shaft 16 is comprised of a tubular inner shaft 80 defining a large interior lumen 82. Extending through the lumen 82 along the entire length of the shaft 80 are multiple optical fibers, best shown in FIG. 4, including first and second illumination fibers 84, 86 and an imaging fiber 88. The fiber 88 terminates at an imaging lens 90 at the distal end face 92 of shaft 80. Also extending through the lumen 82 is a tube 96 which can be used to transfer fluid from luer fitting 28 to an open end of tube 96 substantially coincident with said distal end face 92. The tube 96 can be used to irrigate the valve site to be cut to, for example, optimally orient the valve leaflets or to aspirate material from the site. The distal ends of the tube 96, illumination fibers 84, 86, and imaging fiber 88 all terminate substantially at the distal end face 92 and are consolidated or held together in what may be referred to as a shaft head 98, by suitable potting material 99.

A blade guide member 100 having a central circular opening 102 is mounted on and preferably bonded to the outer surface of tubular inner shaft 80. The guide member 100 defines a pair of oppositely extending lobes 104, 106, and arcuate guide surfaces 108, 110 extending between the lobes. Filament 36 is attached to guide member 100 at 111.

A thin cylindrical ring 120 is also bonded to the outer surface of tubular inner shaft 80 spaced proximally from the blade guide 100. The cylindrical ring 120 functions as a proximal stop for the longitudinal movement of cutting member 34.

The cutting member 34 comprises a substantially cylindrical tube 124 mounted around the outer surface of inner shaft 80 for reciprocal longitudinal movement between the cylindrical ring 120 and the blade guide 100, both fixed to the outer surface of inner shaft 80. The cutting tube 124 is preferably formed by stainless steel and comprises a cylindrical ring 126 whose inner surface 128 is bonded to the outer surface of a push member comprising outer sleeve 130. The sleeve 130 in turn is coaxially supported around the inner shaft 80. The cutting tube 124 includes an inwardly extending flange 132 positioned to engage the cylindrical ring 120 which acts as a stop when the cutting member 124 is moved to its retracted position. The guide member 100 acts as a forward stop when the cutting member is moved to its extended position.

In addition to cylindrical ring 126, the cutting member 124 includes two cantilevered axially extending blades 140, 142. As can be seen in the end view of FIG. 4, the blades 140, 142 are arcuately shaped and define inner arcuate surfaces 144 and 146. The guide surfaces 108, 110 are radially spaced so as to assure engagement against inner blade surfaces 144, 146 respectively. The free distal edges of blades 140, 142 are tapered inwardly to form cutting edges 148, 150 which thus blend into the guide surfaces 108, 110 when the cutting member 124 is in its retracted position, shown in FIG. 3A.

In the retracted position, the cutting member 34 does not extend beyond the distal end face 92. Thus, when the valvulotome shaft 16 is pulled through a vein with cutting member 34 in its retracted position, the view angle through the imaging lens or window 90 is maximized. Additionally, when in the retracted position, the cutting edges 148, 150 lie against the guide surfaces 108, 110, thus protecting the vein wall from damage as the valvulotome is pulled through the vein. Note that to enable the outer surfaces of blades 140, 142 to contact the vein inner wall, all other portions of the valvulotome structure proximate to the distal end are located no further radially outward than the blades.

When the valvulotome distal end face 92 approaches the site of a valve to be cut, the surgeon will view the image captured by the imaging lens 90, via camera coupler 26 at the proximal end. The surgeon will then extend the blades, to orient the two cutting edges 148, 150 with respect to the valve leaflets and will then selectively pull the valvulotome distally, enabling the cutting edges 148 and 150 to cut cleanly through the valve leaflets at the vein wall.

As noted, the distal end of the outer sleeve 130 is bonded to the cutting tube 124. The proximal end of the sleeve 130 extends into the aforementioned handle body 30 and is bonded to the inner wall 151 of an internal cylindrical passage in piston 152. More particularly, with reference to FIG. 5A, note that piston 152 is mounted within cavity 154 of handle body 30 for movement between the retracted position shown in FIG. 5A and the extended position shown in FIG. 5B. The piston 152 is connected to rod 158 which extends up into pin 160. The pin 160 extends through slot 162 in the handle body which enables the pin 160 to move longitudinally with respect to the handle body 30. A flange 164 on the pin 160 lies beneath the wall 166 in which the slot 162 is formed. The upper end of the pin 160 is received in a thumb button 170. An internal spring 172 bears against a washer 174 connected to the pin 162 thus pulling the flange 164 up against the wall 166.

Figure 5A:
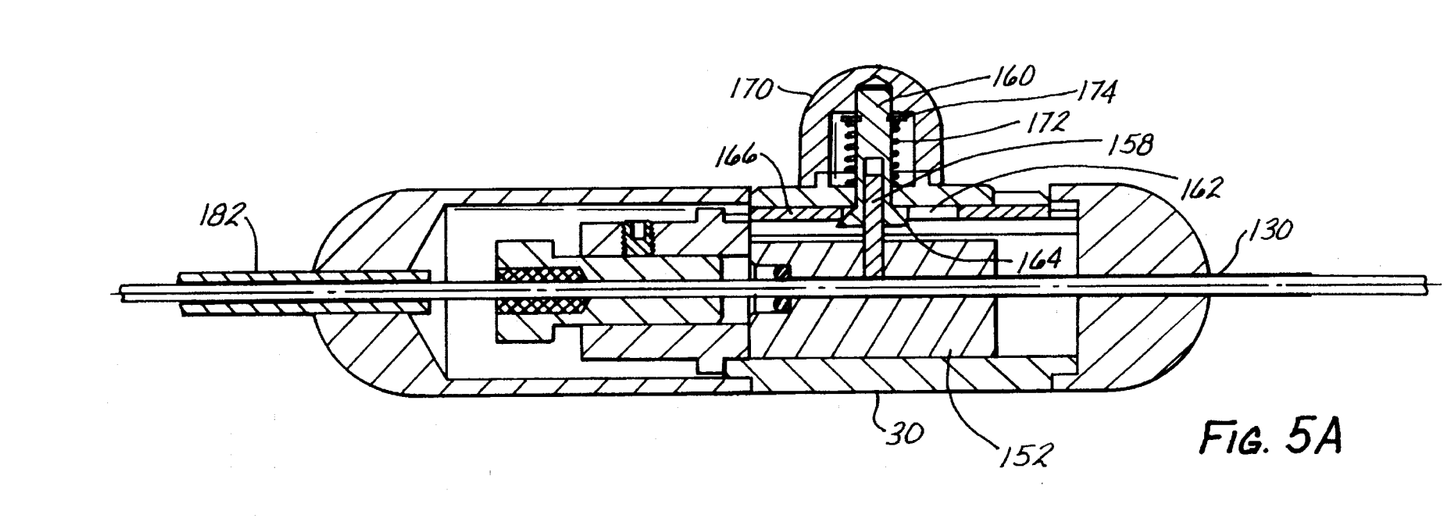
FIGS. 5A and 5B are longitudinal sectional views taken through the actuator handle body showing the slide member in the retracted position and extended position, respectively.
Figure 5B:
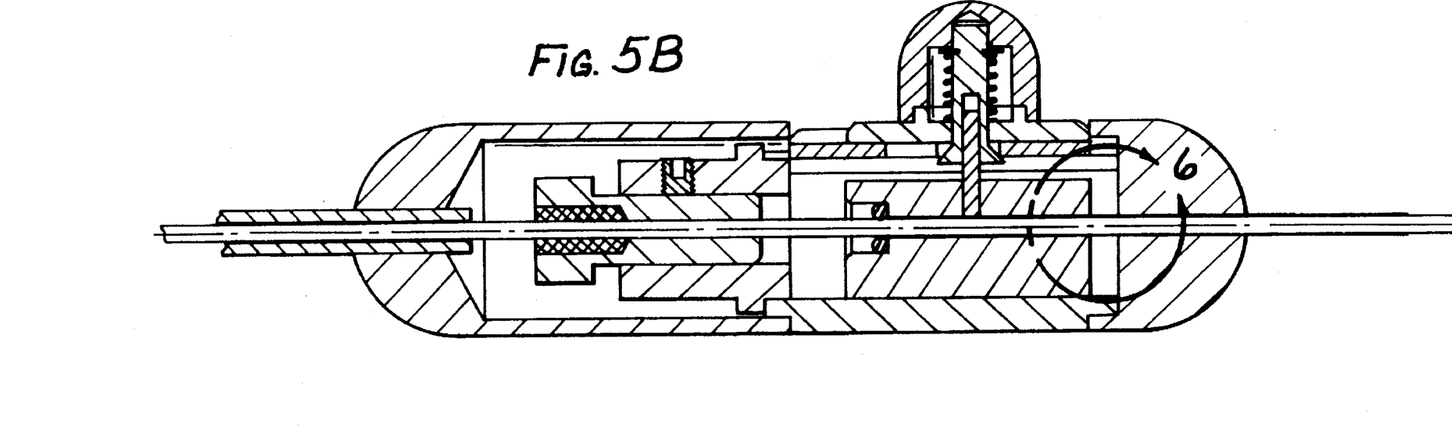
Figure 6:
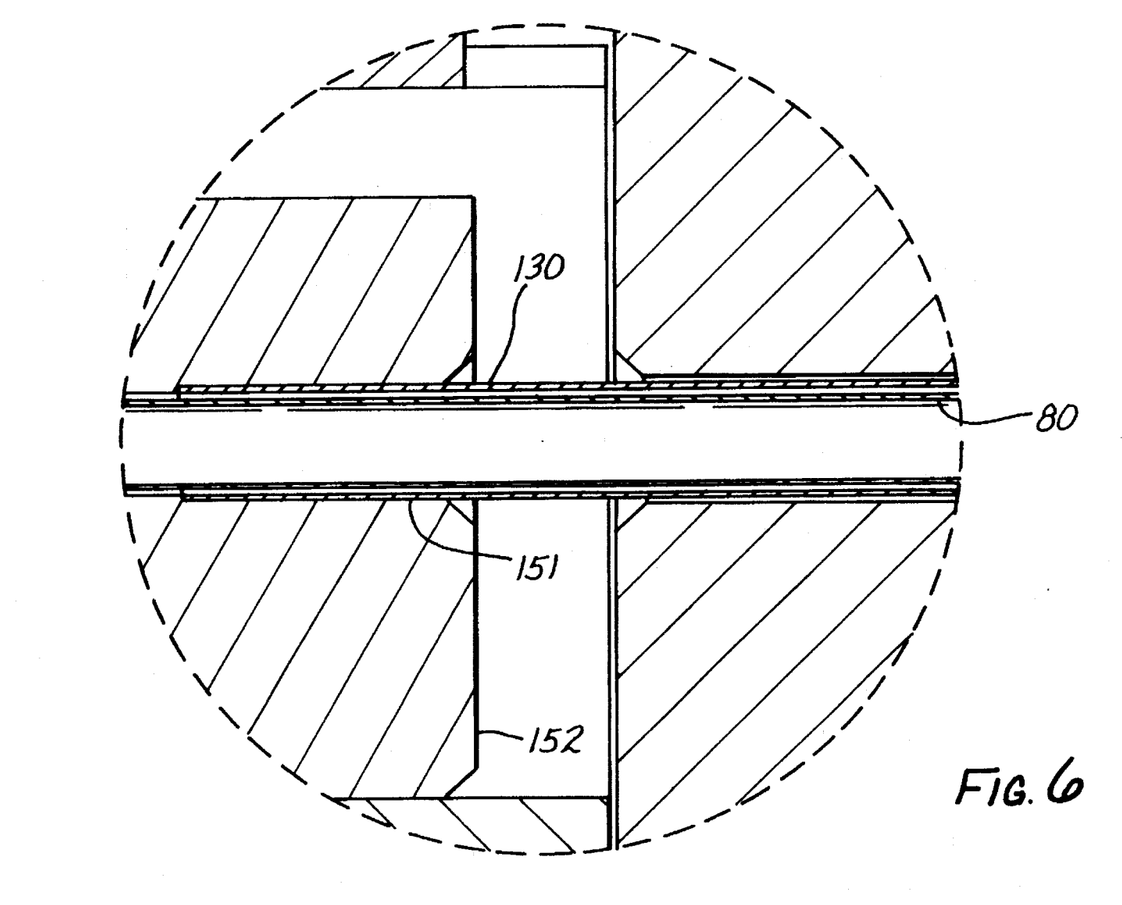
FIG. 6 is an enlarged view showing in detail the portion of the handle body indicated in FIG. 5B.

In use, a surgeon can hold the handle body 30 in his hand and with his thumb, can apply a force to thumb button 170 to slide the piston 152 forwardly from the position of FIG. 5A to the position of FIG. 5B. In so doing, the outer sleeve 130 which is bonded to the piston 152 will move distally along the inner shaft 80.

The inner shaft 80 extends through the handle body 30 and emerges at its proximal end 180, in a sleeve 182 which extends to the aforementioned connector body 22. Within the connector body, the aforementioned illumination fibers 84, 86 are respectively coupled to the light source connector 24, the irrigation channel 96 is coupled to the luer fitting 28, and the imaging fiber 88 is coupled to the camera coupler connector 26.

Figure 7:
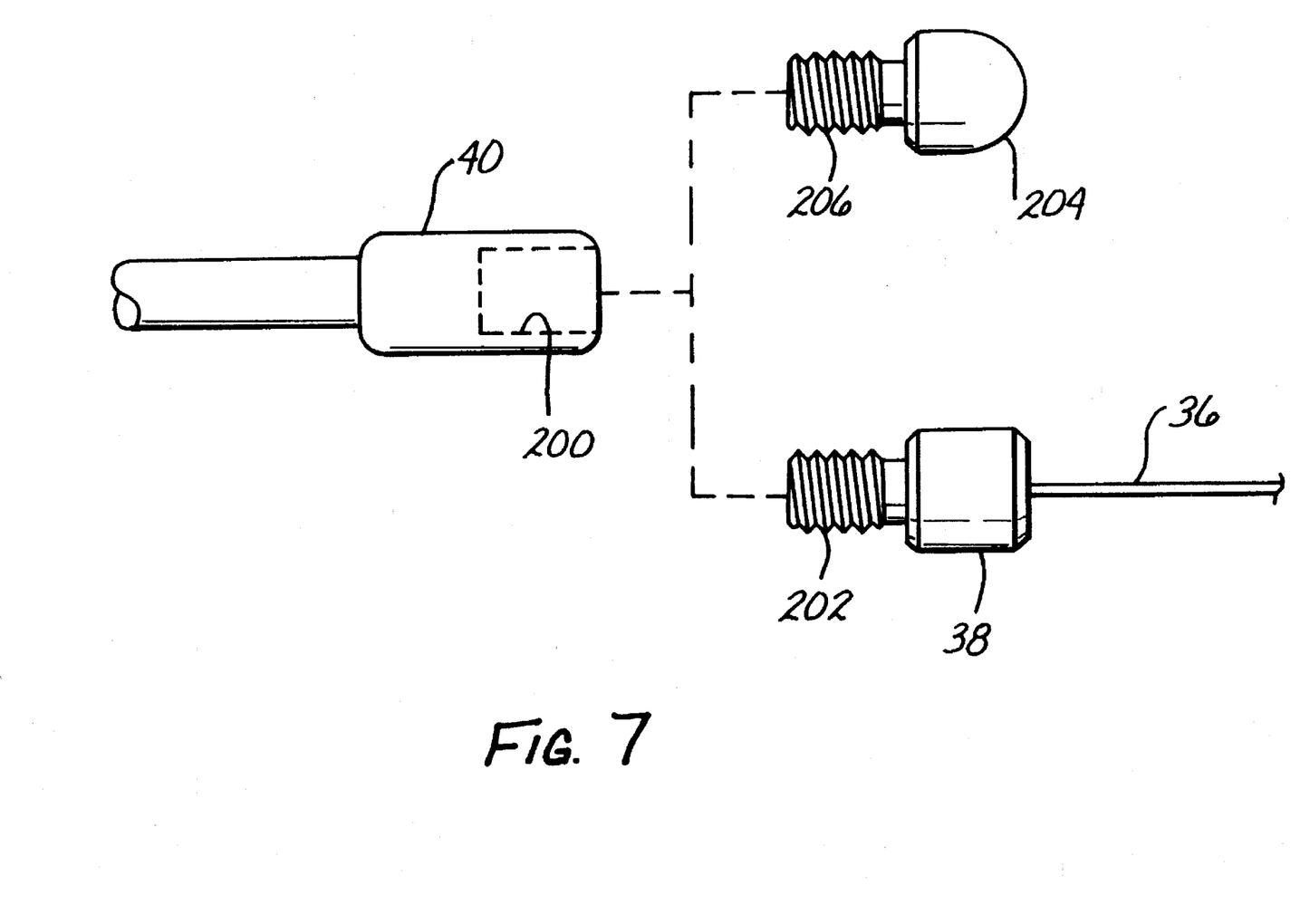
FIG. 7 is a side schematic representation showing a connector members for attaching the valvulotome distal end to the pulling catheter.

Attention is now directed to FIG. 7 which depicts a preferred configuration for valvulotome connector 38 and pulling catheter connector 40. As shown, the connector 40 includes an internal cavity 200 which is threaded to receive an externally threaded male connector 202 attached to the end of valvulotome filament 36. It will be recalled that the other end of filament 36 is attached to the blade guide 100 (FIG. 4) at its periphery 111 to avoid obstructing the surgeon's view of the site to be cut.

FIG. 7 further illustrates an atraumatic tip 204 including a threaded male member 206 receivable in internal cavity 200. The atraumatic tip 204 is used when initially threading the pulling catheter through the vein, as depicted in FIG. 2A, to avoid vein wall damage.

From the foregoing, it should now be appreciated that an improved valvulotome has been disclosed herein characterized by a construction which utilizes a cutting member movable between a retracted and an extended position. In use, the cutting member is normally retained in the retracted position to provide a surgeon with an unobstructed image of the interior of the vein and to enable him to optimally position the blades of the cutting member relative to the valve leaflets to be cut. Additionally, when in the retracted position, the cutting edges of the cantilevered blades of the cutting member are protected by engagement with a guide surface to thereby prevent damage to the vein wall. When the cutting member is properly positioned, the surgeon can then extend the cutting member blades by actuating the slide member button 170 on handle body 30.

We claim:

1. For use with a tubular vein having valve leaflets extending radially inwardly from the inner wall surface of said vein, a valvulotome for threading through said vein and for cutting said leaflets immediately adjacent said vein inner wall surface, said valvulotome comprising:

an elongate flexible shaft having proximal and distal ends, said shaft defining an outer guide surface;

a cutting member comprising a ring having at least one blade cantilevered axially therefrom, said blade defining inner and outer axially extending surfaces and a cutting edge at its free end remote from said ring;

said cutting member ring being externally mounted on said shaft with said blade extending distally and said blade inner surface engaging said guide surface for axial movement relative thereto;

said cutting member including a stop member for limiting said axial movement to a range between a retracted position whereat said cutting edge is proximally positioned and does not extend beyond the shaft's distal end and an extended position whereat said cutting edge is distally positioned and does extend beyond said shaft's distal end, at least part of said cutting member being located radially outward of all other valvulotome structure proximate to said distal end for enabling said blade outer surface, to engage said vein inner wall surface, said blade being movable from said retracted position to said extended position without substantial radial outward movement of said blade relative to said shaft; and a user operable mechanism configured to selectively move said cutting member between said retracted and extended positions.

2. The valvulotome of claim 1 wherein said blade inner surface is arcuately shaped; and wherein said shaft outer guide surface is defined by a guide member mounted on said shaft and including an outer arcuate surface dimensioned to engage said blade inner arcuate surface.

3. The valvulotome of claim 1 wherein said shaft includes an elongate optical fiber extending therethrough defining an imaging window proximate to said distal end.

4. The valvulotome of claim 1 wherein said shaft defines an elongate internal lumen extending therethrough open proximate to said distal end.

5. The valvulotome of claim 1 wherein said user operable mechanism includes:

an elongate sleeve mounted around said shaft for reciprocal longitudinal movement therealong, said sleeve having a distal end attached to said cutting member ring;

a slide member mounted between said shaft's proximal and distal ends; and wherein said sleeve has a proximal end attached to said slide member.

6. The valvulotome of claim 1 including a connector adapted to be detachably attached to a pulling catheter; and a flexible filament connecting said connector to said shaft distal end.

7. For use with a tubular vein having valve leaflets extending radially inwardly from the inner wall surface of said vein, a valvulotome for threading through said vein and for cutting said leaflets immediately adjacent said vein inner wall surface, said valvulotome comprising:

an elongate flexible shaft having proximal and distal ends and defining an outer guide surface proximate to said distal end;

at least one elongate optical fiber extending through said shaft and defining an imaging window proximate to said shaft distal end;

a push member having proximal and distal ends, said push member being mounted for reciprocal movement parallel to the elongation of said shaft;

a cutting member including first and second cutting blades cantilevered axially from the distal end of said push member for movement therewith, said blades defining inner surfaces engaging said outer guide surface and outer surfaces for engaging said vein inner wall surface;

actuator means coupled to said push member selectively operable to move said cutting blades between a retracted position whereat they do not extend beyond said shaft distal end and an extended position whereat they do extend beyond said shaft distal end for cutting said value leaflets, said blades being movable from said retracted position to said extended position without substantial radial outward movement of said blades relative to said shaft, at least part of said cutting member being located radially outward of all other valvulotome structure proximate to said distal end of said shaft; and a stop member for limiting movement of said blades to between said retracted position and said extended position.

8. The valvulotome of claim 7 wherein said shaft defines an internal lumen open proximate to said shaft distal end.

9. The valvulotome of claim 7 wherein said push member comprises a tubular sleeve mounted substantially coaxially with respect to said shaft.

10. The valvulotome of claim 7 wherein said actuator means includes a handle body;

a manually operable slide member mounted in said handle body for reciprocal movement with respect thereto; and means coupling said slide member to said push member proximal end.

11. The valvulotome of claim 7 wherein the proximal end of said optical fiber terminates in an optical coupler; and wherein said actuator means includes a handle body mounted on said shaft between said shaft distal end and said optical fiber proximal end.

12. The valvulotome of claim 11 wherein said push member comprises a tubular sleeve mounted substantially coaxially with respect to said shaft; and wherein said handle body includes a manually operable slide member mounted for reciprocal movement; and means coupling said slide member to the proximal end of said sleeve.

13. The valvulotome of claim 7 wherein said first and second blades are peripherally displaced from one another; and wherein each of said blades has a cutting edge formed on its free distal end tapering toward said outer guide surface.

14. The valvulotome of claim 7 including attachment means mounted at the distal end of said shaft for releasable attachment to a pulling catheter.

15. The valvulotome of claim 14 wherein said attachment means includes a coupler; and a flexible filament securing said coupler to said shaft distal end.

* * * * *